(12) United States Patent
Gerndt et al.

(10) Patent No.: US 7,136,454 B2
(45) Date of Patent: Nov. 14, 2006

(54) METHOD FOR OPERATING AN X-RAY ANALYSIS APPARATUS WITH TWO-DIMENSIONAL ARRAY DETECTOR AND X-RAY ANALYSIS APPARATUS FOR CARRYING OUT THE METHOD

(75) Inventors: Ekkehard Gerndt, Karlsruhe (DE); Michael Jacob, Karlsruhe (DE)

(73) Assignee: Bruker AXS GmbH, Karlsrue (DE)

( * ) Notice: Subject to any disclaimer, the term of this patent is extended or adjusted under 35 U.S.C. 154(b) by 0 days.

(21) Appl. No.: 11/110,900

(22) Filed: Apr. 21, 2005

(65) Prior Publication Data

US 2005/0259790 A1 Nov. 24, 2005

(30) Foreign Application Priority Data

May 21, 2004 (DE) .................. 10 2004 025 121

(51) Int. Cl.
*H05G 1/64* (2006.01)
(52) U.S. Cl. .................. 378/98.12; 378/19
(58) Field of Classification Search .................. 378/19, 378/98.8, 98.11, 98.12, 207; 250/370.08, 250/370.09, 208.1; 382/131, 132
See application file for complete search history.

(56) References Cited

U.S. PATENT DOCUMENTS

| | | | |
|---|---|---|---|
| 5,847,398 A | 12/1998 | Shahar | .................. 250/370.09 |
| 2004/0114707 A1 | 6/2004 | Bruder | .................. 378/4 |

FOREIGN PATENT DOCUMENTS

| | | |
|---|---|---|
| DE | 198 00 946 | 7/1999 |
| DE | 100 43 474 | 3/2002 |
| DE | 100 47 366 | 5/2002 |
| DE | 103 07 752 | 8/2004 |

OTHER PUBLICATIONS

Gerhard Lutz, "Semiconductor Radiation Detectors" Springer-Verlag, Berlin, 2001.
B. Mikulec, "Development of Segmented Semiconductor Arrays for Quantum Imaging", Elsevier Science, Journal Logo, Oct. 2003.
N. Wermes, "Pixel detectors for particle physics and imaging applications", Nuclear Instruments and Methods in Physics Research A 512 (2003), 277-288.
Ch. Broennimann et al., "Status of the Pixel Detector Development", Scientific Report 1998, vol. VII, p. 35.
H. Goebel, "A New Method for Fast XRPD Using a Position Sensitive Detector", Adv. In X-Ray Analysis 22, 81978, 255-265.

*Primary Examiner*—Courtney Thomas
(74) *Attorney, Agent, or Firm*—Paul Vincent

(57) ABSTRACT

A method for operating an X-ray analysis device is characterized by the following steps: a) recording a first data set in a first relative spatial position of a source, an object and a detector; b) displacement and/or rotation of the detector in the detector plane relative to the source and the object, whereby the relative position of source and object is not changed; c) recording a second data set In the position displaced according to step b); and d) superposition of the recorded data sets to form an overall data set, wherein the pixels of the recorded data sets are combined corresponding to their actual relative position with respect to the source and object.

20 Claims, 4 Drawing Sheets

METHOD FOR OPERATING AN X-RAY ANALYSIS APPARATUS WITH TWO-DIMENSIONAL ARRAY DETECTOR AND X-RAY ANALYSIS APPARATUS FOR CARRYING OUT THE METHOD

This application claims Paris Convention priority of DE 10 2004 025 121.5 filed May 21, 2004 the complete disclosure of which is hereby incorporated by reference.

BACKGROUND OF THE INVENTION

The invention concerns a method for operating an X-ray analysis device with an X-ray radiation source, an object under investigation which is irradiated with X-ray radiation, and a planar two-dimensional array detector with pixel elements for locally resolved detection of the X-ray radiation emitted by the object, wherein a data set is obtained, in particular, in the form of a digitized diffractogram and/or spectrum. The invention also concerns an X-ray analysis device for carrying out the method.

Two-dimensional array detectors, which are used in X-ray analysis devices of the above-mentioned type, are known i.a. from Gerhard Lutz "Semi-conductor radiation detectors", B. Mikulec et al. "Development of Segmented Semiconductor Arrays for Quantum Imaging" Elsevier Science, N. Wermes "Pixel detectors for particle physics and imaging applications" Elsevier Science Direct and Edwin M. Westbrook National Institute of Health Förderantrag www.brunel.ac.uk/research/rose/3D/publications.html. These array detectors consist of a plurality of photo-sensitive pixel elements which are arranged in the form of an array on a chip. The sensor chip is usually in bump bonding contact with an ASIC (Application Specific Circuit), which comprises electronic channels, amplifiers and discriminators. Since the photo-sensitive pixel elements are integrally connected to the ASIC, exchange of a faulty pixel element is not possible. Faulty, in particular, blind pixel elements represent a substantial technical problem. Attempts have been made to reduce the number of blind pixel elements through manufacturing improvements. Due to the large complexity of the hybrid production (sensor, bump bonds, highly integrated ASIC), only very expensive pixel detectors with 100% functionality will be available in the near future. One usually accepts the existence of individual blind pixel elements and the resulting missing information in the corresponding regions.

To avoid the resulting disturbing effect of e.g. black image regions (dead pixels), several pixels are conventionally combined into one super pixel. This method, however, reduces the resolution of the associated measurements. If effects on the size of one pixel element are to be observed, individual blind pixel elements can seriously falsify the data, since precisely those dead pixel regions could contain important information.

In addition to two-dimensional array detectors, one-dimensional detectors are also disclosed (H. Göbel, Adv. in X-Ray Analysis 22 (1978) 255–265) which can be displaced using a goniometer through changing the 2Θ value over the region which is of interest for the measurement and permit detection of differing measuring regions by different pixels. However, these methods only permit one-dimensional recordings. Moreover, the optics for focussing the radiation onto the detector must be displaced along with the detector, which disadvantageously requires the structure of the arrangement to be particularly stable.

It is therefore the underlying purpose of the present invention to propose a method for operating an X-ray analysis device having a two-dimensional array detector with pixel elements which reduces the number of or eliminates dead pixels in the data set despite the presence of blind pixel elements in the detector to thereby obtain as complete a data set as possible as well as an X-ray analysis device for carrying out this method.

SUMMARY OF THE INVENTION

This object is achieved in accordance with a method for operating an X-ray analysis device which is characterized by the following steps:
a) recording of a first data set in a first relative spatial position of source, object and detector;
b) displacement and/or rotation of the detector relative to the source and the object in the plane of the detector, wherein the relative position of source and object is not changed;
c) recording a second data set in the position displaced according to step b);
d) superposition of the recorded data sets to form an overall data set, wherein the pixels of the recorded data sets are combined corresponding to their actual position relative to the source and object.

Displacement of the detector between the recordings of two data sets causes displacement of the faulty pixel elements relative to the object under investigation such that the radiation emitted by the object which has impinged on faulty pixel elements in the first recording, after displacement, will most likely be incident on a photo-sensitive pixel element during recording of the second data set. Superposition of the two recorded data sets permits more efficient detection of X-ray radiation and reduction of the number of dead pixels in the overall data set.

In a preferred variant of the inventive method, steps b) and c) are repeated once or several times with varying displacement, before step d). The number of dead pixels in the data set can thereby be arbitrarily reduced.

In a further development of this variant, the data sets are recorded during a continuous, preferably periodic displacement and/or rotation of the detector. The overall data set comprises data integrated between two positions of the detector.

Through displacement and/or rotation of the detector, preferably less than 10 pixels are swept between two data set recordings to realize a maximum overlap of the regions with multiple measurements.

In a particularly preferred method variant, the detector is displaced by exactly one pixel element between two recordings of sequential data sets.

A further object of the invention is to propose a method for operating an X-ray analysis device which permits measurement of a data set with a resolution which is better than the dimensions of the individual pixel elements.

In a further variant of the inventive method, the detector is displaced between two recordings of subsequent data sets by a fraction, preferably 1/n of a pixel element, wherein n is a positive integer, preferably n<10. This displacement of the detector by a sub pixel increases the spatial resolution, which is particularly advantageous for detectors with large pixel elements or for recording very small structures. The resolution of the detector is thereby improved in such a manner that structures within a pixel element can be detected. To obtain a uniform resolution over the entire detector region, n displacements must be carried out with their corresponding recordings.

In an advantageous variant of the method, the detector is displaced in different directions in the plane of the detector. The detector may be displaced within the entire detector surface to facilitate optimization with regard to the position of the dead pixels.

In the inventive method, some regions of the data set, in particular, the edge regions are recorded less frequently than the central region of the data set. For this reason, the pixels of the edge regions of the overall data set which are not included in the data sets of all individual recordings, are advantageously weighted in step d) corresponding to the inverse of their recording frequency. One obtains an average signal intensity for each pixel.

In a particularly preferred variant of the inventive method, each pixel element is assigned an individual sensitivity and/or a statistical error and/or an offset for the recorded measured value which are considered in step d) in weighting of the respective pixels when the recorded data sets are superposed. The recordings of the individual data sets are thereby not falsified through the varying sensitivity and/or the statistical error or through an offset.

The individual recorded data sets are preferably superposed such that the offset is subtracted for each data point to be superposed, the measured value is normalized corresponding to the sensitivity of the respective pixel element and is weighted inversely to the magnitude of the associated statistical error, wherein the overall weighting for each pixel is 1 or 100%.

In a variant of the inventive method, the contributions of individual pixel elements are fixedly weighted with 0 during superposition of the data sets in step d), in particular of defective pixel elements which are known to be blind, generate greatly fluctuating signals or always display their saturation value. Due to the greatly falsifying effects of such pixel elements, it is advantageous to weight them with 0 and extract the values of the corresponding pixels for the overall data set from the remaining data sets.

To avoid dead pixels in the overall data set, each pixel must be recorded at least once by a pixel element having a value other than 0. For this reason, the trajectories of the respective displacements are advantageously adjusted to the spatial distribution of the faulty pixels elements, in particular, such that, if possible, no data point of the overall data set exclusively consists of a superposition of signal contributions of faulty pixel elements.

For manufacturing reasons, the detector advantageously comprises several sensor chips which border each other at blind edge regions, wherein the blind edge regions are treated like faulty pixel elements. Although detectors combined in this fashion, have many non-photo-sensitive regions, the inventive method permits recording of overall data sets which have no holes due to the missing active pixel elements at the corresponding edge regions of the sensor chips.

The trajectories of the respective displacements are preferably selected to minimize the statistical error of the overall data set. In this manner, dead pixels or pixels weighted with 0 can be distributed to a maximum number of different positions and double blind measurements can be avoided.

The invention also concerns an X-ray analysis device with a source for X-ray radiation on an object to be investigated which is irradiated with X-ray radiation, and a planar two-dimensional array detector with pixel elements for spatially resolved detection of X-ray radiation emitted by the object, whereby a data set, in particular, in the form of a digitized diffractogram and/or spectrum is obtained. The inventive X-ray analysis device is characterized in that it comprises means for a) recording a first data set in a first relative spatial position between source, object and detector;
b) displacement and/or rotation of the detector in the detector surface relative to the source and the object, wherein the relative position of source and object is not changed;
c) recording a second data set in the position displaced according to step b);
d) superposition of the recorded data sets to form an overall data set, wherein the pixels of the recorded data sets are combined corresponding to their actual relative position with respect to the source and object.

The X-ray analysis device is preferably designed to carry out the above-described method.

In a preferred embodiment of the inventive X-ray analysis device, a piezo drive is provided to displace the detector. A piezo drive effects displacements on a µm scale and below which allows almost any detector displacement.

In a further embodiment of the X-ray analysis device, the array detector is movably disposed together with a first stage of an evaluation electronics on a carrier which is not moved during the measurement, wherein the first stage is electrically connected to a further stage of the evaluation electronics via a flexible connection to transmit signals. In this manner, a fast pre-amplifier may be disposed very close to the detector thereby improving the signal-to-noise ratio. The flexible connection between the first stage and a further stage of the evaluation electronics ensures movability of the detector.

In a further development of the inventive X-ray analysis device, the flexible connection comprises a thin sheet, preferably a polyimide sheet with integrated conductor paths.

In a particular embodiment of the inventive X-ray analysis device, the width B of the blind edge regions is an integer multiple of the width b of a pixel element. The data points missing in the first individual data set due to the non-sensitive edge regions can then be obtained through displacement of the detector by an integer number of pixel elements.

Further advantages of the invention can be extracted from the description and the drawing. The features mentioned above and below may be used individually or collectively in arbitrary combination. The embodiments shown and described are not to be understood as exhaustive enumeration but have exemplary character for describing the invention.

DESCRIPTION OF THE PREFERRED EMBODIMENT

Figure 1:
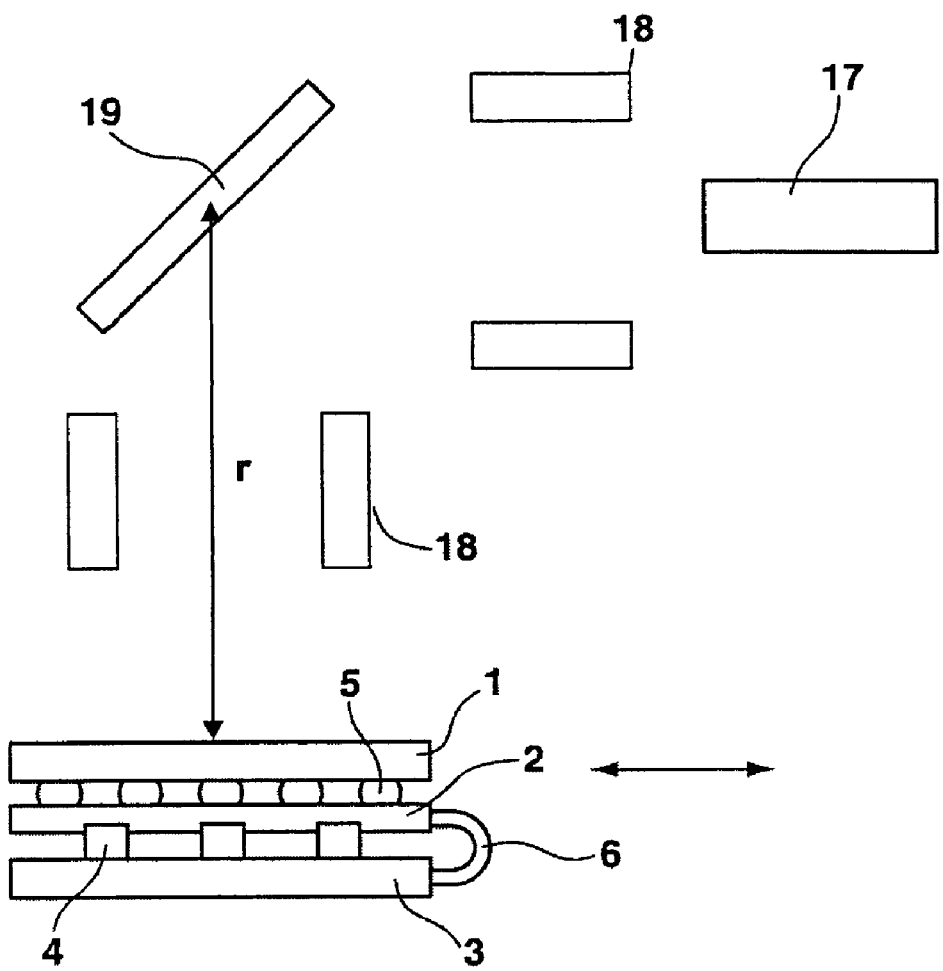
FIG. 1 shows a schematic illustration of the essential elements of an X-ray analysis device with an inventive array detector.

FIG. 1 schematically shows the essential elements of an X-ray analysis device. The X-ray radiation emitted by a source 17 is modified using optical elements 18 and subjects an object 19 to particular X-rays. In Bragg-Brentano, the X-ray is e.g. focussed onto the detector using optical elements 18. The X-ray radiation emitted by the object 19 is detected using an inventive array detector. The radiation may be scattered, transmission or diffraction radiation. The array detector is provided with an X-ray sensitive individual detector 1, a first stage 2 of an evaluation electronics (ASIC), a carrier 3 and a piezo drive 4, wherein the individual detector 1 contacts the first stage 2 of the evaluation electronics and is rigidly connected thereto via bumps 5. The connection between individual detector 1 and carrier 3 is realized by a flexible connection 6 which contains electric connections between the first stage 2 of the evaluation electronics and a further stage of the evaluation electronics which may be located e.g. on the carrier 3. The individual detector 1 with first stage 2 of the evaluation electronics may be displaced relative to the carrier 3 and an object 19 in the plane of the individual detector 1 through application of an electric voltage to the piezo elements of the piezo drive 4. The piezo drive 4 permits extremely precise displacements with small stroke and high speed. In accordance with the invention, the entire detector is not displaced, merely the individual detector portion 1 with the first stage 2 of the evaluation electronics connected thereto. The mass of the components to be displaced is thereby minimized to ensure rapid and simple displacement using the piezo drive 4. Moreover, the accompanied displacement of the first stage 2 of the evaluation electronics permits low-noise pre-amplification and subsequent digital processing of the detected signals thereby obtaining a good signal-to-noise ratio. The individual detector 1 is thereby displaced in one or in two dimensions such that the radial separation r of the individual detector 1 relative to the object 19 does not change. The movement is indicated by an arrow. Focussing to a new plane is therefore not necessary. Although the individual detector 1 of FIG. 1 has a planar construction, curved embodiments are also feasible. The X-ray radiation sensitive pixel elements 7 (not indicated in this drawing) of the individual detector 1 typically consist of Si or other semiconducting materials such as e.g. GaAs, CdTe, CZT. The evaluation electronics 2 is typically implemented in CMOS or Bi-CMOS technology, e.g. having structural sizes of 0.35 µm.

Figure 2:
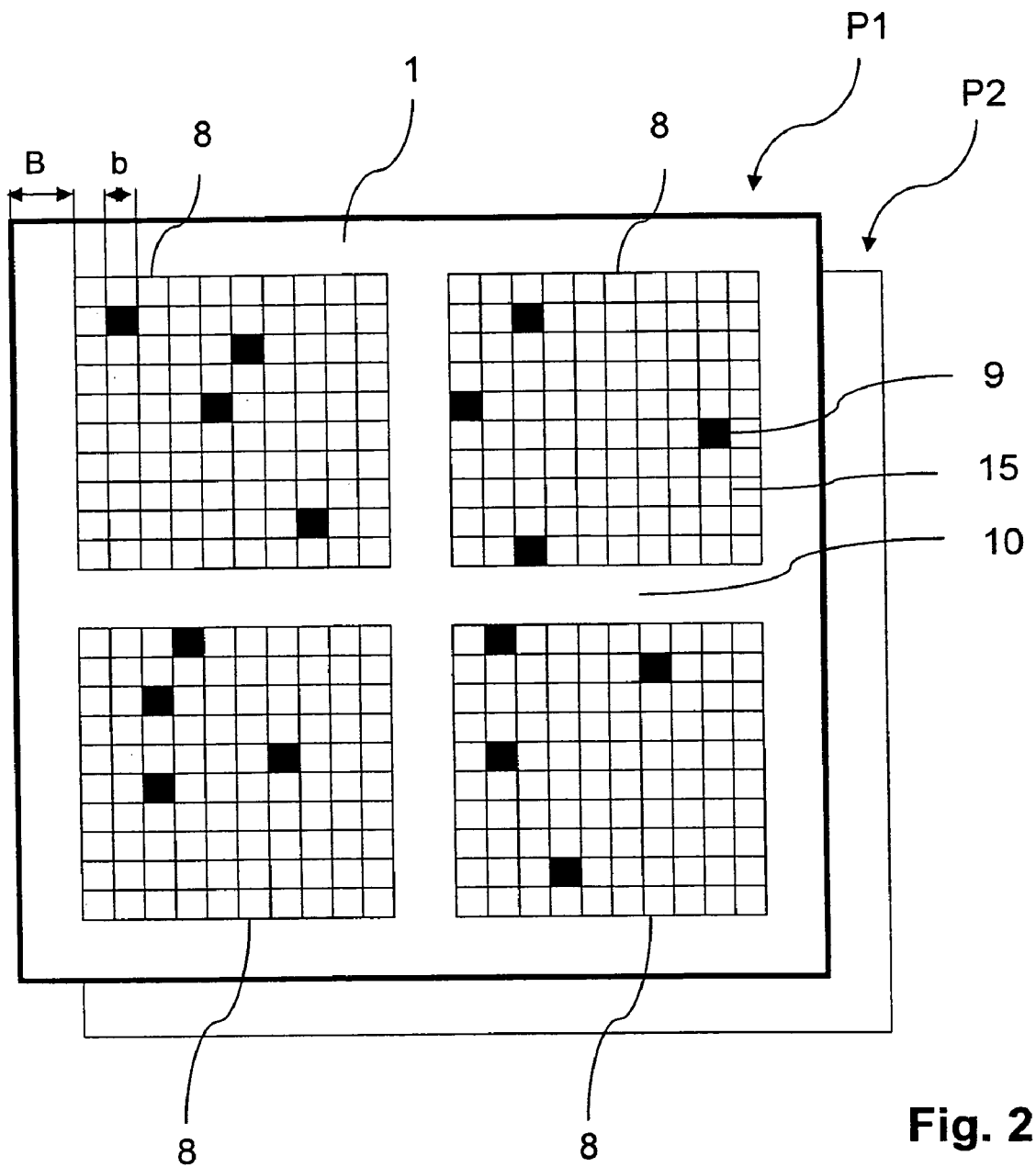
FIG. 2 shows an individual detector which consists of several sensor chips with faulty pixel elements.

FIG. 2 shows an overall detector 1. Since the conventional individual sensor chips 8 are generally smaller than the desired individual detector surface, the individual detector 1 is composed of several sensor chips 8 with the result that, in addition to the faulty pixel elements 9 contained in the sensor chips, edge regions 10 of the sensor chips 8 are additionally located within the individual detector surface which give no information for the data set to be recorded. The faulty pixel elements 9 and also the edge regions 10 of the sensor chips 8 therefore produce dead pixels 12a, 12b in a recorded data set 11. To prevent falsification of information within a data set 11, faulty pixel elements 9 in the data set are weighted with 0. In addition to blind pixel elements, this also includes pixel elements which generate highly fluctuating signals or signals which permanently reach their saturation value. Pixel elements of this type can be identified in a calibration measurement. Common sensor chips comprise approximately 1,000×1,000 pixel elements. For reasons of simplicity, the sensor chips 8 shown in FIG. 2 only have 10×10 pixel elements.

Figure 3A:
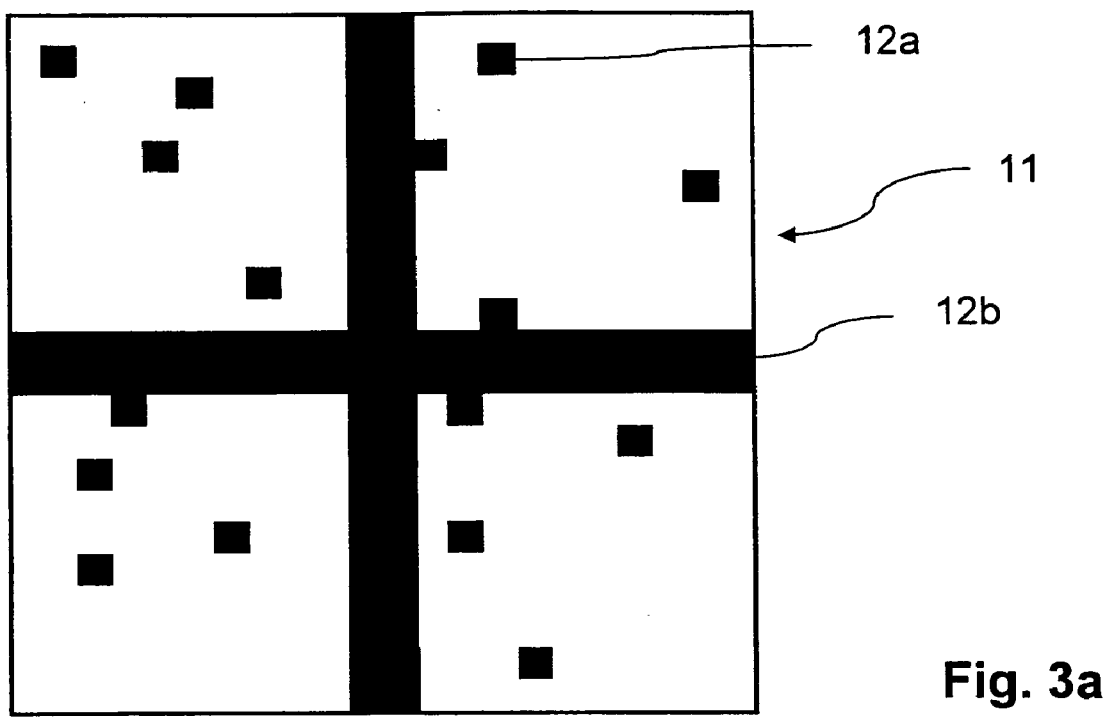
FIG. 3a shows a schematic illustration of the distribution of dead pixels in a data set recorded with the individual detector of FIG. 2.

FIG. 3a shows a schematic illustration of the distribution of dead pixels 12a, 12b in a data set 11 which was recorded by an individual detector 1 as shown in FIG. 2. In addition to the isolated dead pixels 12a which result from the faulty pixel elements 9 of the individual detector 1, one can clearly see the disturbing effects of the edge regions 10 of the sensor chips 8 which appear in the form of strips of dead pixels 12b in the data set 11. To avoid such negative edge effects, high-energy physics conventionally disposes the sensor chips 8 in a stepped geometry such that the edge region 10 of an individual detector 8 is covered by a further individual detector 8. In this manner, the size of the overall edge regions 10 is at least reduced. This is, however, not practicable if the radiation to be detected must be focussed into a particular plane as is required e.g. in the Bragg-Brentano geometry of X-ray diffractometry.

In the inventive method, the sensor chips 8 are therefore disposed in a plane. After a first recording of a first data set in a position P1, the individual detector 1 is displaced from this position P1 into a position P2 (FIG. 2). In position P2, a further data set 11 is recorded which is superposed with the first data set 11 to obtain an overall data set 13. In the inventive method, the width B of the blind edge regions of the sensor chips 8 is preferably an integer multiple of the width b of a pixel element, wherein the width b of a pixel element is on the order of magnitude of 50 to 100 µm. In this manner, a pixel element in position P1 can be disposed to be completely coincident with a pixel element in position P2 through displacement of the individual detector 1 by an integer multiple of pixel elements 7.

Figure 3B:
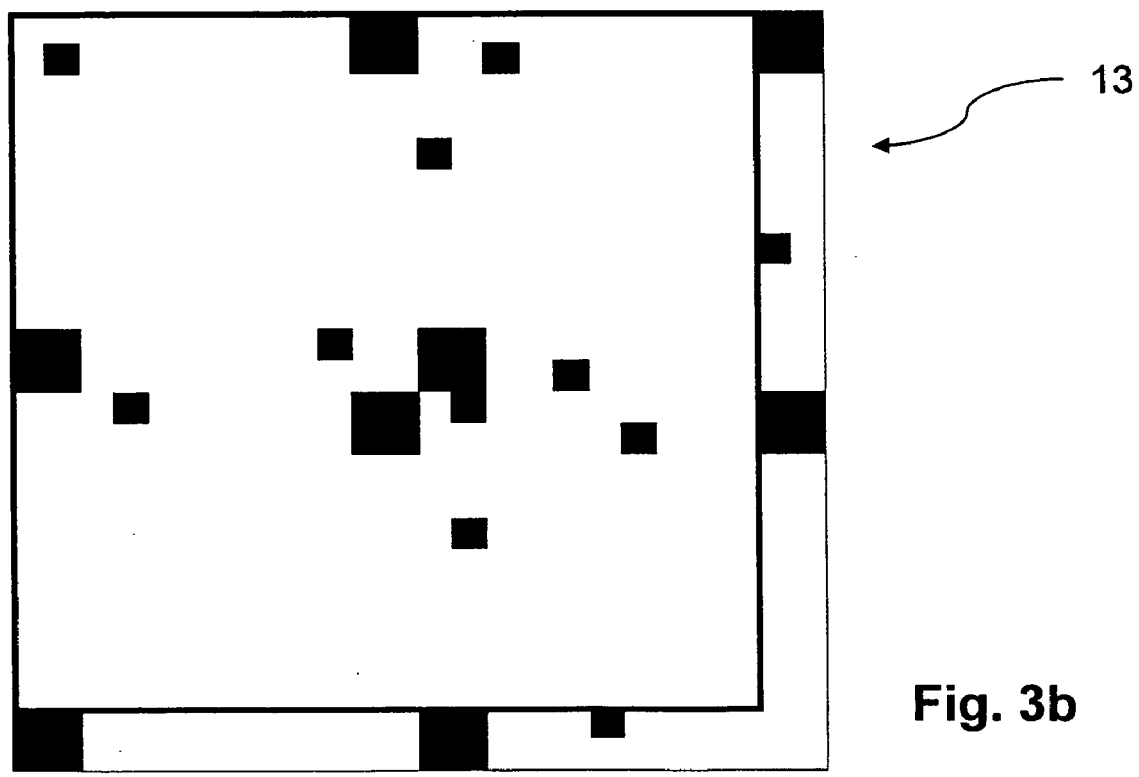
FIG. 3b shows a schematic illustration of the distribution of dead pixels in an overall data set which was obtained through superposition of two individual data sets recorded with the individual detector of FIG. 2.

FIG. 3b shows the distribution of the dead pixels 12 in the overall data set 13 which is obtained from the data sets 11 of the measurements in positions P1 and P2. Displacement of the individual detector 1 is arbitrarily selected and was 2×2 pixel elements. This overall data set 13 shows that the number of dead pixels 12 is considerably reduced compared to the number of dead pixels 12a, 12b in the data set 11 of FIG. 3. If the displacement of the individual detector 1 is suitably optimized, the dead pixels 12 in the overall data set 13 can be further reduced, in the ideal case down to zero dead pixels 12. The result may also be improved through recording further data sets 11 in different positions of the individual detector 1 and their superposition into an overall data set 13. Since the measuring time is prolonged due to recording of several data sets 11, when carrying out the inventive method, the predetermined measuring time can be selected to be sufficiently long to permit recordings of the individual data sets 11. For XRD (X-ray diffraction), this can be realized in most cases without any problems to permit optimum utilization of the advantages of the invention.

The different sensitivities of the individual pixel elements 7 are taken into consideration through weighting of the individual pixels when the individual data sets are superposed. Each pixel element may also be associated with a statistical error and an offset for the recorded measured value, which are taken into consideration in weighting of the respective pixels when the recorded data sets 11 are superposed. The offset of the data points to be superposed is thereby subtracted, the measured value is normalized corresponding to the sensitivity of the respective pixel element 7 and is weighted inversely with respect to the magnitude of the associated statistical error to obtain an overall weighting of 1 or 100% for each pixel.

In addition to the sensor chips shown in FIG. 2 which are provided with equivalently sized pixel elements 7, there are also conventional sensor chips having larger pixel elements in their edge regions (super pixel elements). These super pixel elements reduce the resolution in these areas. This undesired effect is also eliminated by the inventive method, since, with suitable displacement of the sensor chips 8, those regions which were previously measured by the super pixel elements are measured, during at least one further measurement, by a photo-sensitive pixel element 15, thereby obtaining a more homogeneous spatial resolution over the entire detector surface.

FIG. 3b also shows that the measured region of the overall data set 13 (thin border line) is larger than that region detected by the data set 11 (thick border line). The inventive method therefore reduces disturbing influences of the edge regions 10 within an individual detector 1, reduces dead pixels 12 in the overall data set 13 and also increases the recording region.

Figure 4:
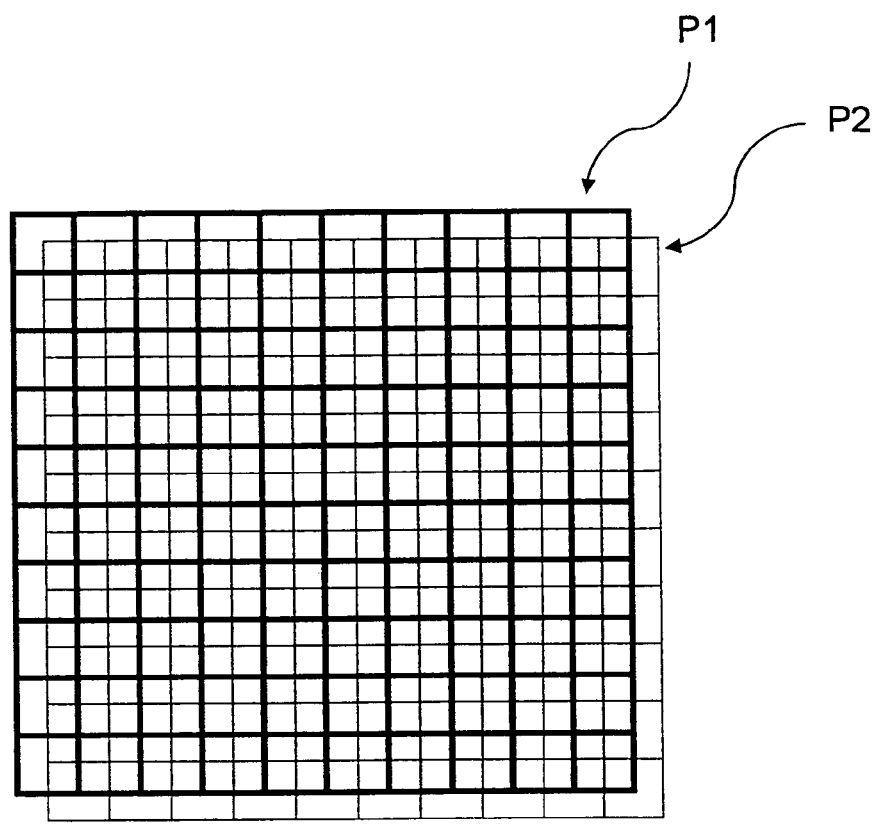
FIG. 4 shows displacement of an array detector by a sub pixel element.

For technical and financial reasons, pixel detectors having a rough structure are often used whose number of channels can be reduced. However, their spatial resolution is insufficient for many applications. The inventive method permits use of such inexpensive pixel detectors with rough structure with improved spatial resolution, as is schematically shown in FIG. 4. A rectangular individual detector 8 with rough structure is displaced by one sub pixel element after recording a first data set in a position P1 (wide frame), in the present case, by half a pixel element 7 and diagonally to a position P2 (thin border line). This permits detection of signal changes within one pixel thereby increasing the spatial resolution of the overall data set.

The advantages of the invention are particularly useful in a combination of one or more displacements by an integer multiple of a pixel element 7 with one or more subsequent displacements by a sub pixel. This leads to an overall data set with a reduced number of dead pixels 12, ideally zero, and an improved spatial resolution using a conventional individual detector 1.

Figure 5:
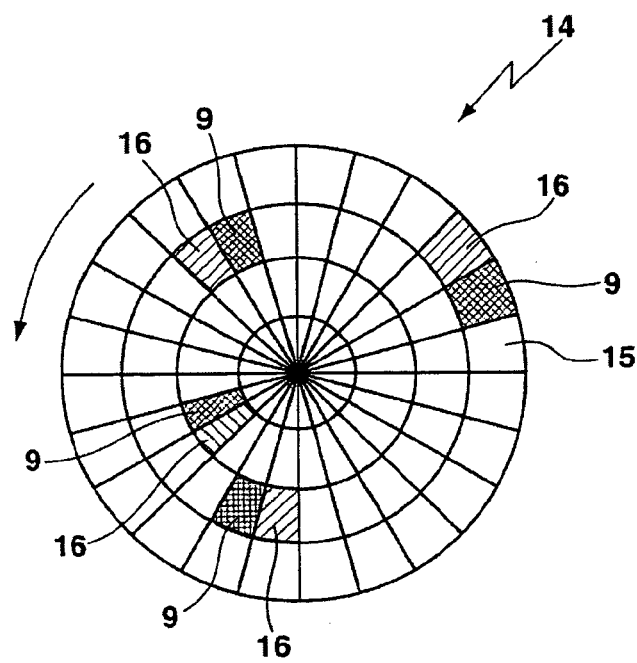
FIG. 5 shows displacement of faulty pixel elements of a rotationally symmetric individual detector.

The application of the inventive method is not limited to rectangular sensor chips 8. Radially symmetric sensor chips 14 with annular segments as pixel elements (FIG. 5) may also be used for this method. Displacement is thereby preferably effected through a rotary motion about the center of the radially symmetric individual detector 14. To calculate or optimize displacement, polar coordinates are preferably used for such radially symmetrical sensor chips. The faulty pixel elements 9 or those weighted with 0 are displaced to neighboring locations 16 such that the dead pixels of the first data set are measured in the second data set using photo-sensitive pixel elements 15 thereby constructively contributing to the overall data set.

The inventive X-ray analysis device or the inventive method for operating an X-ray analysis device permits straightforward reduction of dead pixels in the data set which are generated due to faulty pixel elements or pixel elements weighted with 0, in particular, without displacement of the optical elements which belong to the X-ray analysis device. The use of individual detectors combined from several sensor chips also eliminates disturbing influences of the edge regions when data sets are generated. The recording region is also increased and the spatial resolution of the measurement is improved by suitable displacement of the individual detector.

LIST OF REFERENCE NUMERALS 1 individual detector consisting of one or more sensor chips 8
2 first stage of an evaluation electronics
3 carrier
4 piezo drive
5 bumps
6 flexible connection
7 pixel elements
8 sensor chip
9 faulty pixel elements
10 edge region
11 data set
12 dead pixels
13 overall data set
14 radially symmetric individual detector
15 photo-sensitive pixel elements
16 locations of the displaced faulty pixel elements
17 x-ray radiation source
18 optical elements
19 object
P1 first position
P2 second position
B width of the blind edge regions
b width of a pixel element

We claim:

1. A method for operating an X-ray analysis device, the device having a source for X-ray radiation, an object under investigation which is irradiated with X-rays from the source, and a two-dimensional array detector with pixel elements for spatially resolved detection of the X-rays emitted by the object, wherein a data set, a digitized diffractogram, and/or a spectrum is obtained, the method comprising the steps of:
   a) recording a first data set in a first relative spatial position among the source, the object, and the detector;
   b) displacing and/or rotating the detector, in a detector surface, relative to the source and the object, wherein a relative position between the source and the object is not changed;
   c) recording a second data set following step b); and
   d) superimposing the first and the second recorded data sets to form an overall data set, wherein pixels of the first and the second recorded data sets are combined corresponding to their actual positions relative to the source and the object.

2. The method of claim 1, further comprising repeating, prior to step d), steps (b) and (c) once or several times with varying displacement.

3. The method of claim 2, wherein a plurality of data sets are recorded during continuous, periodic displacement and/or rotation of the detector.

4. The method of claim 1, wherein less than 10 pixel elements are swept between said first and said second data sets recordings through displacement and/or rotation of the detector.

5. The method of claim 4, wherein the detector is displaced between the first and the second recordings of the data sets by exactly 1 pixel element.

6. The method of claim 4, wherein the detector is displaced by a fraction of a pixel element or by 1/n of a pixel element between the first and the seconds recordings, wherein n is a positive integer or a positive integer <10.

7. The method of claim 2, wherein the detector is displaced in different detector surface directions.

8. The method of claim 2, wherein in step d), pixels of edge regions of the overall data set to which the data sets of some individual recordings do not contribute, are weighted corresponding to an inverse of their recording frequency.

9. The method of claim 1, wherein each pixel element is individually associated with a sensitivity, a statistical error, and/or an offset for the recorded measured value, which are considered in step (d) in weighting of a respective pixel during superposition of the first and second recorded data sets.

10. The method of claim 9, wherein the first and the second recorded data sets are superposed such that an offset is subtracted for each data point to be superposed, a measured value is normalized corresponding to a sensitivity of a respective pixel element and weighted inversely with respect to a magnitude of an associated statistical error, wherein each pixel has an overall weighting of 1 or 100%.

11. The method of claim 9, wherein contributions of certain pixel elements are fixedly weighted with zero when the first and second data sets are superposed in step d) or are weighted with zero for faulty pixel elements which are known to be blind, to generate highly fluctuating signals, or to permanently display their saturation values.

12. The method of claim 11, wherein trajectories of respective displacements are adjusted to a spatial distribution of faulty pixel elements or are adjusted such that as few data points as possible consist exclusively of superposed signal contributions of faulty pixel elements.

13. The method of claim 11, wherein the detector is composed of several sensor chips bordering via blind edge regions, and the blind edge regions are treated as faulty pixel elements.

14. The method of claim 1, wherein trajectories of respective displacements are selected such that an overall statistical error of the overall data set is minimized.

15. An X-ray analysis device with an X-ray radiation source for irradiating an object under investigation with X-ray radiation, a two-dimensional array detector with pixel elements for spatially resolved detection of the X-ray radiation emitted by the object to obtain a data set or a data set which is a digitized diffractogram or a spectrum, the device comprising:

means for recording a first data set in a first relative spatial position among the source, the object, and the detector;

means for displacing and/or mtating the detector, in a detector surface, relative to the source and the object without changing a relative position between the source and the object;

means for recording a second data set in a second relative spatial position among the source, the object, and the detector; and means for superimposing the first and the second data sets to form an overall data set, wherein pixels of the first and the second recorded data sets are combined corresponding to their actual positions relative to the source and the object.

16. The X-ray analysis device of claim 15, further comprising means for repeating varying detector displacement and recording of data sets prior to superposition of all recorded data sets to form the overall data set.

17. The X-ray analysis device of claim 15, wherein a piezo drive is provided to displace the detector.

18. The X-ray analysis device of claim 15, wherein the array detector, together with a first stage of an evaluation electronics, is movably disposed on a carrier which does not move during measurement, wherein the first stage is electrically connected to a further stage of the evaluation electronics via a flexible connection for transmitting signals.

19. The X-ray analysis device of claim 18, wherein the flexible connection comprises a thin sheet or a polyimide sheet, with integrated conductor paths.

20. The X-ray analysis device of claim 15 wherein a width B of the blind edge regions is an integer multiple of a width b of a pixel element, each pixel element being individually associated with a sensitivity, a statistical error, and/or an offset for the recorded measured value, which are considered in weighting of a respective pixel during superposition of the first and second recorded data sets, wherein contributions of certain pixel elements are fixedly weighted with zero when the first and second data sets are superposed or are weighted with zero for faulty pixel elements which are known to be blind, to generate highly fluctuating signals, or to permanently display their saturation values, said detector being composed of several sensor chips bordering via blind edge regions, the blind edge regions being treated as faulty pixel elements.

* * * * *